United States Patent [19]
Grant

[11] 3,955,944

[45] May 11, 1976

[54] CONTROLLED SELECTIVITY ACTIVATED CARBON

[75] Inventor: Richard John Grant, Pittsburgh, Pa.

[73] Assignee: Calgon Corporation, Pittsburgh, Pa.

[22] Filed: Nov. 8, 1974

[21] Appl. No.: 521,992

Related U.S. Application Data

[60] Division of Ser. No. 402,682, Oct. 2, 1973, Pat. No. 3,884,830, which is a continuation-in-part of Ser. No. 132,217, April 7, 1971, abandoned.

[52] U.S. Cl. .................................................. 55/74
[51] Int. Cl.² ........................................ B01D 53/04
[58] Field of Search ............. 55/74, 75, 76; 127/55; 252/444, 445, 421; 201/8

[56] References Cited
UNITED STATES PATENTS

| | | | |
|---|---|---|---|
| 2,763,580 | 9/1956 | Zabor | 127/55 |
| 2,909,579 | 10/1959 | Schmidt | 55/76 |
| 3,479,300 | 11/1969 | Rivin | 252/444 X |
| 3,483,134 | 12/1969 | Olson et al | 252/444 X |
| 3,884,830 | 5/1975 | Grant | 252/421 |

Primary Examiner—Theodore A. Granger
Attorney, Agent, or Firm—Harry E. Westlake, Jr.; Raymond M. Speer

[57] ABSTRACT

A series of fast acting activated carbons is made having high surface areas and at the same time very small pore size. The method of manufacturing them, which specifies certain carbonaceous starting materials and pulverizing, agglomerating, crushing and oxidizing steps, determines or controls the pore sizes and surface areas. My activated carbon has highly uniform, very small pore sizes and at the same time a large surface area per unit of weight and a large macropore volume. New methods of separating mixtures of compounds, such as mixtures of hydrocarbons, are disclosed employing my new molecular sieve activated carbon. In my fast-adsorbing molecular sieve, molecules of generally lower molecular weight are adsorbed by the carbon rather than the usual case for activated carbon, which is that the carbon tends to adsorb generally larger molecules in preference to smaller ones.

3 Claims, No Drawings

CONTROLLED SELECTIVITY ACTIVATED CARBON

This application is a division of co-pending application Ser. No. 402,682, filed Oct. 2, 1973 now U.S. Pat. No. 3,884,830, which was a continuation-in-part of co-pending application Ser. No. 132,217, filed Apr. 7, 1971, now abandoned.

BACKGROUND OF THE INVENTION

The term "molecular sieve" is applied to certain compositions because of their most useful property—the ability to separate mixtures of compounds with which they are contacted. The better known natural zeolites which were first used for such purposes include chabazite, faujasite, and analcite. Chabazite is a natural zeolite having the ability, for example, to adsorb unbranched hydrocarbons while rejecting branched hydrocarbons and, hence, is referred to as a molecular sieve.

The classical molecular sieve, whether natural or synthetic, exhibits certain properties which are undesirable for many purposes. For example, a zeolitic molecular sieve is not chemically inert, it has polar surface characteristics (i.e., is hydrophilic), may be adversely affected by high temperature, and may be comparatively expensive. Insofar as the properties of a molecular sieve are determined by physical adsorption, the term "sieve" is misleading, since there is no separation of "rejected" and "passed" materials as in a screen or sieve; one or more components of the mixture treated is adsorbed and the rest are not adsorbed.

Granular activated carbon is normally thought of as having a mesh size in a range of, perhaps, 4 × 10 to 20 × 50 U.S. Sieve Series. It will have a surface area (determined by the adsorption of $N_2$) of at least 600 square meters per gran but generally not more than about 1,300 square meters per gram and may adsorb an amount of carbon tetrachloride equivalent to about 50 percent of its weight. The surface area is roughly a measure of the capacity of the carbon and is conventionally determined by the quantity of iodine adsorbed. A discussion of a commercial activated carbon and its characteristics may be found in Zabor's U.S. Pat. No. 2,763,580.

Prior to the present invention, activated carbons had been prepared which exhibited molecularly selective properties not usually observed. See, for example, Walker, P. L.; Lamond, T. G.; and Metcalfe, J. E., 2d Conf. on Industrial Carbon and Graphite (1965). The authors used commercial activated carbons, coated them with significant amount of certain resins, and carbonized them at temperatures ranging from 500°C to 850°C. Comparisons were then made with commercial synthetic zeolitic molecular sieves. See, also, Evans and Flood, U.S. Pat. No 3,516,791 and Konrad, U.S. Pat. No. 2,790,511.

M. M. Dubinin et al, reporting in *Nature*, V. 207, P. 75–76 (July 3, 1965), prepared an activated carbon from wood which exhibited pore size properties comparable to zeolitic or synthetic molecular sieves but which had very low surface areas. J. E. Metcalfe III, M. Kawahata, and P. L. Walker, Jr., applied the term "molecular sieve" to certain activated anthracite coals, indicated to have a low surface area. [Fuel, 42, 233 (1963)].

W. F. K. Wynne-Jones, in the proceedings of the Tenth Symposium of the Colston Research Society, P. 35 (1958), studied the surface area of activated carbon and made comparisons to commercial zeolitic synthetic molecular sieves.

Activated carbons made from such source material as polyvinylidene chloride, polyvinylbenzene, urea-formaldehyde resins, etc., have exhibited properties which have not found general use. See for example, J. J. Kipling and R. B. Watson, "Adsorptive Properties of Polymer Carbons," Trans Faraday Society 56, 557, 562 (1960); J. R. Dacey and D. G. Thomas "Adsorption on Saran Charcoal" Trans Faraday Society 50, 647, 740 (1954); Mahajan and Walker, "Krypton Adsorption on Microporous Carbons and 5A Zeolite," *J. Colloid and Interface Science*, V. 29, No. 1, P. 129 (1969).

SUMMARY OF THE INVENTION

A more or less conventional description of activated carbon may include a measure of pore volume in terms of, for example, carbon tetrachloride adsorption. The carbon tetrachloride number may also represent the uniformity of pore opening; that is, the number of pores having openings large enough to admit the carbon tetrachloride molecule. The conventional description may also include a measure of surface area per unit of weight as determined by iodine adsorption. I have developed a series of activated carbons having carbon tetrachloride numbers of less than 2 and at the same time iodine numbers greater than 450.

The iodine number is defined as the milligrams of iodine adsorbed from an aqueous iodine-potassium iodide solution by one gram of pulverized activated carbon when the iodine concentration of the residual filtrate is 0.02 normal.

The procedure is a follows. Place 1.000 gram of dried pulverized carbon into a flask; add 10 ml. of 5 percent weight hydrochloric acid and swirl until carbon is wetted. Place flask on hotplate, bring contents to boil and allow to boil for only 30 seconds. After allowing the flask and contents to cool to room temperature, add 100 ml. of standardized 0.1 normal iodine solution to the flask. Immediately stopper the flask and shake contents vigorously for 30 seconds. Filter by gravity through an E&D No. 512 folded filter paper. Discard the first 20 or 30 ml. of filtrate and collect the remainder in a clean beaker. Do not wash the residue on the filter paper. Mix the filtrate in the beaker with a stirring rod and pipette 50 ml. of the filtrate into a flask. Titrate the 50 ml. sample with standardized 0.1 normal sodium thiosulfate solution until the yellow color has almost disappeared. Add about 2 ml. of starch solution and continue titration until the blue indicator color just disappears.

Calculate the iodine number as follows:

$$\frac{X}{m} = \frac{A - (2.2B \times \text{ml. of thiosulfate solution used})}{\text{weight of sample (grams)}}$$

$$C = \frac{N_2 \times \text{ml. of thiosulfate solution used}}{50}$$

Iodine number = $X/m \cdot [1,295 - 20.51C + 286.4C^2]$ $X/m$ = mg. iodine adsorbed per gram of carbon $A = N_1 \times 12693.0$ $B = N_2 \times 126.93$ $C$ = residual filtrate normality $N_1$ = normality of iodine solution $N_2$ = normality of sodium thiosulfate solution The capacity of a carbon for any adsorbate is dependent on the concentration of the adsorbate in the medium contacting the carbon. Thus, the concentration of the residual filtrate must be specified, or known, so that appropriate factors may be applied to correct the concentration to agree with the definition.

The amount of sample to be used in the determination is governed by the activity of the carbon. If the residual filtrate normality (C) is not within the range 0.008N to 0.035N, the procedure should be repeated using a different size sample.

It is important to the accuracy of the test that the potassium iodide to iodine weight ratio is 1.5 to 1.0 in the standard iodine solution.

The iodine solution is prepared as follows. Dissolve 12.7 grams of reagent grade iodine and 19.1 grams of potassium iodide in distilled water. Dilute to one liter in a volumetric flask. To standardize the iodine solution, pipette 25.0 ml. into a 250 ml. Erlenmeyer flask and titrate with the standardized 0.1 N sodium thiosulfate. Use the starch indicator when the iodine fades to a light yellow color. Then finish the titration by adding the thiosulfate dropwise until a drop produces a colorless solution.

In the test for carbon tetrachloride activity, dry air subsequently saturated with carbon tetrachloride vapor is passed through a bed of granular carbon until there is no further increase in the weight of the carbon. The percentage increase in weight of the carbon is the "carbon tetrachloride activity."

I have found that the highly activated carbon of this invention having the desirable physical and performance characteristics of a fast acting, highly selective molecular sieve can be prepared by the techniques hereinafter described from relatively inexpensive and commercially available starting materials. Bituminous coal and charred naturally occurring carbonaceous materials such as coconut char, lignite char, petroleum acid sludge char, charred nut shells and wood char all may be employed as raw materials in the preparation of the molecular sieve carbon having the desired properties. My invention, however, does not contemplate the use of chars derived from synthetic carbonaceous materials such as polyvinylidene chloride.

In preparing the molecular sieve activated carbon of this invention, I pulverize the coal or the other carbonaceous material such as coconut char to a mesh size wherein at least 65 percent of the pulverized material will pass through a 325 mesh screen. The pulverized coal then is mixed with about 5 to 15 percent by weight of pitch or other carbonaceous binder, which is also pulverized, and the mixture is agglomerated or formed by mild compression into shapes which, in turn, are crushed and screened. As will be seen by data presented herein, it is preferred that a relatively narrow mesh size distribution be used. This pulverization, agglomeration and crushing pre-treatment of the raw material prior to activation is an important aspect of my invention. I have found that such pretreatment introduces macroporosity into the finished product which leads to an activated carbon which is significantly more fast acting than are activated carbons prepared from non-agglomerated raw materials. Further, when bituminous coal is employed as the raw material, the agglomeration pre-treatment inhibits undesirable coke formation.

The granular material thus obtained then is air baked at a temperature of from 300°C to 400°C for a period of 120 to 360 minutes. Desirably, the granular material is introduced into a baking zone pre-heated to a temperature about 100°C to 150°C below the desired activation temperature (i.e. 150°C to 250°C) and the temperature in the baking zone then gradually brought up to the desired activation temperature over a period of 45 to 60 minutes. Particularly where the raw material is coal, such gradual rise to activation temperature inhibits undesirable coke formation. Charred naturally-occurring carbonaceous materials such as those mentioned above are not prone to coking during activation and when these substances are employed as the starting material they may be introduced into the baking zone at the activation temperature without the gradual temperature rise described above.

Air is introduced into the baking zone in quantities providing totals of about 5 to 8 liters of air to be contacted with a gram of carbon. The quantity of air used is the product of the air flow and the baking time during which air is introduced. The quantity of air (or oxygen) actually contacting the carbon may be varied as desired by varying either of these factors.

Calcination then is performed. The granular material is introduced to a calcining zone at a temperature of from 850°C to 960°C and holding the granular material within that range for a period of from 5 to 20 minutes. Usually however, calcination will be completed within a period of 5 to 10 minutes. The purpose of the calcination step is to drive off such elements as are volatile under the conditions of the calcination step.

The activated carbon thus made should have an iodine number (representing surface area) of at least 450 and a carbontetrachloride number (representing pore size) of no greater than 2.0. The combined properties of very high surface area, very low pore size and fast action render this activated carbon particularly useful for purposes usually associated with molecular sieves rather than activated carbon.

A generally preferred preparation of the feed material may be described as follows. The raw coal or charred naturally-occurring carbonaceous material first is pulverized to 85 to 90 percent — 325 U.S. Sieve Series. Then 5 to 15 percent pitch is added in the pulverizer (usually on the high side for coconut or other chars and on the low side for coal). The mixture is then briquetted or agglomerated and subsequently crushed to a granular mesh of about 12 to 30. This material then is activated by the method described above.

Typical examples of the preparation of various samples of the activated carbon of this invention are shown in Table 1 below. In the preparations of these examples, a bituminous coal was employed as the raw material. The coal was pulverized in a micropulverizer. It then was intimately mixed in the micropulverizer with about 7 percent particulate coal tar pitch having a softening point in the range of 90°C to 100°C and formed into briquettes at a pressure of 20,000 psi and at a temperature up to about 110°C. The briquettes then were crushed and screened to the desired mesh sizes. Activation of the granules took place in air at the temperatures and for the times shown in the table. The product was then calcined for seven minutes at a temperature of 850°C to 960°C in a partially closed container in a muffle furnace. The devolatilization process which takes place during calcination has a significant effect on surface area and carbontetrachloride activity.

Table 4 below. High temperatures and air flow rates result in over-activation, i.e., $CCl_4$ numbers in excess of 2.0.

TABLE 1

| No. | Mesh Size | Gram Wt. of Sample Charge | Air Flow l/Min | Temperature Point 1°C | 2°C | 3°C | Time Min | $I_2$ | $CCl_4$ |
|---|---|---|---|---|---|---|---|---|---|
| 1 | 18×30 | 50 | 3.0 | 370 | 370 | 360 | 120 | 443 | 0.78 |
| 2 | 14×18 | 50 | 3.0 | 380 | 380 | 380 | 180 | 511 | 0.84 |
| 3 | 14×18 | 50 | 3.0 | 380 | 380 | 380 | 180 | 487 | 0.53 |
| 4 | 18×30 | 50 | 3.0 | 360 | 360 | 360 | 180 | 469 | 0.63 |
| 5 | 10×14 | 50 | 3.0 | 360 | 360 | 360 | 180 | 508 | 0.48 |
| 6 | 14×18 | 50 | 4.0 | 370 | 360 | 370 | 180 | 526 | 0.92 |
| 7 | 14×18 | 50 | 4.0 | 360 | 360 | 360 | 180 | 479 | 0.70 |
| 8 | 10×14 | 50 | 3.0 | 360 | 360 | 360 | 180 | 465 | 0.39 |
| 9 | 10×14 | 50 | 3.0 | 370 | 370 | 370 | 180 | 528 | 0.30 |
| 10 | 14×18 | 100 | 4.0 | 450 | 450 | 450 | 300 | 541 | 14.0 |
| 11 | 14×18 | 100 | 4.0 | 360 | 360 | 360 | 360 | 477 | 5.7 |
| 12 | 14×18 | 100 | 4.0 | 350 | 350 | 350 | 360 | 512 | 1.9 |
| 13 | 10×14 | 100 | 4.0 | 360 | 360 | 340 | 360 | 479 | 0.69 |
| 14 | 10×14 | 100 | 4.0 | 350 | 350 | 360 | 240 | 570 | 2.6 |
| 15 | 10×14 | 100 | 4.0 | 350 | 350 | 350 | 360 | 467 | 1.3 |
| 16 | 10×14 | 100 | 6.0 | 350 | 350 | 350 | 240 | 513 | 4.5 |
| 17 | 10×14 | 100 | 3.0 | 350 | 350 | 350 | 360 | 481 | 1.5 |
| 18 | 10×14 | 100 | 4.0 | 360 | 360 | 360 | 270 | 485 | 1.0 |
| 19 | 14×18 | 100 | 6/1 | 340 | 340 | 350 | 230 | 429 | 0.0 |
| 20 | 14×18 | 100 | 4/1 | 350 | 360 | 350 | 320 | 461 | 0.12 |
| 21 | 14×18 | 100 | 3/1 | 360 | 360 | 350 | 280 | 457 | 0.1 |
| 22 | 10×14 | 100 | 3 | 360 | 360 | 350 | 340 | 481 | 1.14 |
| 23 | 10×14 | 100 | 3 | 350 | 360 | 350 | 310 | 473 | 0.27 |
| 24 | 10×14 | 100 | 3 | 370 | 380 | 370 | 270 | 516 | 0.91 |
| 25 | 10×14 | 100 | 3 | 350 | 370 | 370 | 270 | 501 | 0.57 |
| 26 | 14×18 | 100 | 3 | 360 | 380 | 380 | 270 | 548 | 2.0 |
| 27 | 14×18 | 100 | 3 | 360 | 380 | 330 | 185 | 496 | 0.69 |

From the data in Table 2, it may be assumed that for a given yield coconut raw material requires less oxygen in the initial activation step than coal, since the quantity of air consumed is considerably less than that for coal to achieve a comparable level of activation. The combination temperatures and times in Table 2 were the same as for Table 1. The material used was coconut char agglomerated with 15 percent pitch. It was treated in a 2-inch rotary furnace.

TABLE 2

Activation of Agglomerated Coconut Char

| No. | Mesh Size | Gram Wt. of Sample Charge | Air Flow l/Min. | Furnace Temp. °C | Time Min. | $I_2$ | $CCl_4$ |
|---|---|---|---|---|---|---|---|
| 1 | 12×20 | 50 | 2.0 | 340 | 130 | 504 | 0.0 |
| 2 | 12×20 | 50 | 2.0 | 340 | 130 | 504 | 1.1 |
| 3 | 12×20 | 50 | 2.0 | 340 | 130 | 572 | 1.5 |
| 4 | 12×20 | 50 | 2.0 | 340 | 130 | 502 | 1.0 |

Table 3 shows the effect of retention time in the activation step at a given temperature. It will be seen that the iodine number and the $CCl_4$ number both increase with the retention time. Yield decreases due to increased oxidation.

TABLE 3

Effect of Retention Time
Conditions: 50 grams, 10×30 mesh, 2 liters air per minute, activation temperature 340°C

| Retention Time Runs | Iodine Number | $CCl_4$, Wt. % | Yield Percent |
|---|---|---|---|
| 90 | 352 | 0.2 | 81.6 |
| 130 | 470 | 0.3 | 80.0 |
| 150 | 516 | 0.5 | 78.0 |
| 180 | 486* | 0.75* | 70.0* |

*Average of 2 runs

The effect of an increase in activation temperature roughly parallels that of retention time, as shown in

TABLE 4

Effect of Activation Temperature
Conditions: 50 grams, 14×18 mesh, 3 liters air per minute, retention time, 180 minutes, 10.8 liters air per gram

| Activation Temperature, °C | Iodine Number* | $CCl_4$, Wt. %* | Yield Percent* |
|---|---|---|---|
| 300 | 350 | 0.28 | 92.2 |
| 320 | 410 | 0.23 | 87.0 |
| 340 | 420 | 0.28 | 84.8 |
| 350 | 440 | 0.50 | 79.5 |
| 360 | 446 | 0.40 | 77.1 |
| 370 | 466 | 0.63 | 69.5 |
| 380 | 500 | 0.70 | 67.1 |

*Average of 2 runs

The process of devolatilization which takes place during the calcination step causes a "shrinkage" of the pores (reflected in a decreased carbon tetrachloride number) and an increase in the micropore volume and surface area, the latter being reflected in an increased iodine number. Although the surface area must be increased significantly during the calcination step, the temperatures and times required to assume the desired results are statistically difficult to relate. For example, the effect of variations in calcination temperature was studied in the laboratory using three different calcination temperatures for seven minutes, with the results shown below in Table 5.

TABLE 5

Effect of Calcination Temperature

| Calcination Temperature, °C | Iodine Number | $CCl_4$, Wt.% | Calcination Yield Percent |
|---|---|---|---|
| 863 | 426 | 0.25 | 70 |
| 898 | 396 | 0.24 | 68 |
| 953 | 348 | 0.5 | 70 |

It could be assumed from Table 5 that the $CCl_4$ number is not particularly affected by the calcination temperature in the general range of 860°C to 960°C. More complete studies made later illustrate better the somewhat improved $CCl_4$ number which accompanies increases of temperatures through this range while preserving the effect on the iodine number. See Table 6.

TABLE 6

Effect on Iodine and Carbon Tetrachloride
Number of Calcination Temperature and Time

| Sample | Temperature °C | Time (Minutes) | Iodine Number | $CCl_4$ Number |
|---|---|---|---|---|
| A | 863 | 7 | 513 | 1.9 |
| A | 898 | 7 | 477 | 1.2 |
| A | 953 | 7 | 418 | 0.37 |
| B | 863 | 7 | 498 | 2.2 |
| B | 898 | 7 | 443 | 0.8 |
| B | 953 | 7 | 418 | 0.78 |

The effect of mesh size is illustrated in Table 7; the coarser 10 × 14 tends to exhibit higher surface areas as shown by the iodine number and smaller pore size as shown by $CCl_4$ numbers. It is theorized that a greater portion of combustion tends to take place on the outside surface of the smaller granules due to the greater surface/volume ratio. For this reason, a relatively uniform mesh size distribution is desirable. The effect of mesh size may also be seen in Table 1.

TABLE 7

Effect of Mesh Size
Conditions: 50 grams, 3 liters air per minute, retention time, 180 minutes, 10.8 liters air per gram, activation temperature 360°C

| Mesh Size | Iodine Number* | $CCl_4$ Wt. Percent* | Yield Percent* |
|---|---|---|---|
| 10×14 | 486 | 0.43 | 78.0 |
| 14×18 | 446 | 0.40 | 77.1 |
| | Activation temperature 370°C | | |
| 10×14 | 528 | 0.3 | 71.8 |
| 14×18 | 466* | 0.63* | 69.5* |

*Average of 2 runs

As noted above, the agglomeration steps employed in the preparation of the molecular sieve activated carbons of this inventon constitute an important aspect of the invention leading to activated carbon which displays a significantly improved rate of adsorption as compared to activated carbon prepared without agglomeration. Further, the agglomeration has been found to inhibit undesirable coke formation during activation, especially where bituminous coal is employed as the raw material. These effects are illustrated and confirmed in the following experiments. Four samples were prepared for testing:

Sample A consisted of bituminous coal, crushed and screened to 12 × 40 mesh (all mesh sizes mentioned are U.S. Sieve Series).
Sample B consisted of bituminous coal, pulverized to 90 percent through 325 mesh, mixed and mulled with pitch to the extent of 7.5 percent by weight of coal, briquetted at ambient temperature in Carver press, then crushed and screened to 12 × 40 mesh.
Sample C consisted of coconut char, crushed and screened to 12 × 40 mesh.
Sample D consisted of coconut char, pulverized to 90 percent through 325 mesh, mixed and mulled with pitch to the extent of 15% by weight of char, briquetted hot in a Carver press (dietemperature 160°C). then crushed and screened to 12 × 40 mesh.

The samples were subjected to similar processing conditions. Fifty (50) gram samples were oxidized and carbonized in a 2-inch I.D. rotary kiln. The preset kiln temperature was 200°C (392°F). Upon loading the temperature dropped to about 150°C (300°F); the temperature was then programmed up to 340°C (644°F) over 45 minutes, corresponding to a temperature rise of 5°C (8°F) per minute. The temperature was held at 340°C for the remainder of the run. The total run time was three hours. In the case of coal samples A and B, the air flow rate was 4 liters per minute, or 14.4 liters air per gram. In the case of coconut char, the air flow rate was only one-half that used with coal because of the expected higher reactivity of the char.

After the oxidation step, the samples were removed from the kiln, cooled down in a closed container and weighed. They were calcined for 20 minutes at 1450°F in a muffle furnace, the vessel in which they were contained having vent holes to permit escape of pyrolysis products but exclude air. After calcination the samples were cooled down in the absence of air and reweighed. The overall yield was calculated from the results.

Control tests such as apparent density, iodine number, carbontetrachloride number and n-heptane capacity (g/100g carbon) were determined on the samples as shown in Table 8.

TABLE 8

| Sample No. | A.D. g/cc | Yield (%) | $I_2$ No. | $CCl_4$ No. | n-Heptane g/100 g |
|---|---|---|---|---|---|
| A | — | 67.8 | — | — | 0.0 |
| B | 0.609 | 52.4 | 479 | 0.25 | 8.3 |
| C | 0.596 | 60.8 | 566 | 1.71 | 3.2 |
| D | 0.514 | 56.0 | 576 | 0.42 | 4.3 |

Micropore size distributions were determined on the granular samples by the molecular probe method at P/P = 0.5 using n-heptane, 2-methyl pentane and 2,2,4-trimethyl pentane as probes corresponding to 4.6, 5 and 6A, respectfully. The distributions are shown in Table 9.

TABLE 9

CHARACTERIZATION OF MOL SIEVE CARBONS BY MOLECULAR PROBE METHOD

| Sample | n-heptane | | 2-methyl pentane | | 2,2,4 trimethyl pentane | |
|---|---|---|---|---|---|---|
| | g/100 g | cc/100 g | g/100 g | cc/100 g | g/100 g | cc/100 g |
| B | 8.3 | 12.1 | 2.7 | 4.1 | 0.0 | 0.0 |
| C | 3.2 | 4.7 | 1.3 | 1.9 | 0.1 | 0.14 |
| D | 4.3 | 6.3 | 0.9 | 1.3 | 0.07 | 0.1 |

Sample A, consisting of the granular coal, produced, after the calcination step, a fused mass of coke. It had no adsorption capacity. The n-heptane capacity of the material before calcination also was zero. This result is due to the slow rate of oxidation which was far from complete in the time allotted.

Sample B, the agglomerated coal, was a satisfactory molecular sieve carbon, with an iodine number of 479, a carbontetrachloride number of 0.25 wt. -% (Table 8), and a pore structure in the proper range (Table 9). It is apparent, therefore, that pulverizing and agglomerating the coal prior to activation provided access to the interior of the granule, permitting air to enter and the oxidation products to escape and permitted formation of a highly activated carbon without coke formation.

Sample C, the granular coconut char, does not have to oxidize to prevent coking. Even at one-half the air flow a molecular sieve activated carbon was produced with a considerably higher iodine number than the coal. Iodine numbers are determined on pulverized samples, the other tests on granular.

Sample D, the agglomerated coconut char, was a product similar to Sample C with respect to iodine number, carbontetrachloride number and micropore size distribution (Tables 8 and 9).

n-Butane adsorption rate was determined on the granular activated carbon at 25°C and one atmosphere pressure using a Cahn RG vacuum microbalance. The n-butane adsorption rate, in terms of the capacity reached at 40 minutes, is shown in Table 10

TABLE 10

| SAMPLE NO. | ADSORPTION RATE - N-Butane, 25°C, 1 Atm. Percent of Capacity at 40 Minutes | | | | | |
|---|---|---|---|---|---|---|
| | 1 Min | 2 Min | 3 Min | 8 Min | 20 Min | 40 Min |
| B | 70.5% | 80.5% | 85.5% | 93.5% | 97.5% | 100% |
| D | 46.5% | 61% | 69% | 83% | 93% | 100% |
| C | 38.5% | 50.5% | 58% | 74.5% | 89% | 100% |

It can be seen from the foregoing results, that Sample C, the granular coconut char, had a slower rate of adsorption than the agglomerated coconut char (Sample D) even though both were similar in iodine number, carbontetrachloride number and micropore size distribution. Agglomeration in Sample D resulted in significant enhancement of the rate of adsorption.

At the same time, the agglomerated coconut char, Sample D, exhibited a slower adsorption rate than the agglomerated coal, Sample B. This is believed to be due to the finer micropore structure of the coconut char as reflected in the micropore size distribution (Table 9) and the higher iodine number (Table 8). The granular nonagglomerated coal, Sample A, coked and did not yield an activated carbon.

Thus, it may be seen that the instant invention provides a highly activated carbon having properties not heretofore attainable; specifically, it has a high surface area ($I_2 > 450$ milligrams/gram) and a small pore size ($CCl_4 < 2.0$ — less than two grams $CCl_4$ per 100 grams activated carbon).

Such carbon may be used to great advantage to selectively adsorb molecules of a given size while rejecting all others. It is therefore useful as a molecular sieve.

My "controlled selectivity" activated carbon has several distinct advantages over the synthetic molecular sieves and/or the natural zeolitic molecular sieves. Activated carbon has no "ionizable" charge sites and is otherwise chemically inert to most chemicals and conditions. While zeolitic molecular sieves may isomerize a normal hydrocarbon (one of the uses of zeolitic molecular sieves) the controlled selectivity activated carbon will not do so. The controlled selectivity activated carbon will adsorb a normal hydrocarbon from a mixture with isomers, and the hydrocarbon is recoverable through known processes. Branched fatty acids, alcohols, alkyl sulfates, etc., can be separated from their normal straight chain counterparts with controlled selectivity activated carbon. Its capacity is equivalent to that of commercial synthetic molecular sieves. Recovery of adsorbates may be accomplished by thermal swing, pressure swing, solvent displacement, and other known methods. Where recovery is not needed, the carbon can be regenerated by hot inert gas, superheated steam, air activation at, for example, 400°C, or any other method known to be effective for activated carbon.

I do not intend to be bound by or restricted to any theories or examples above. My invention may be otherwise variously practiced within the scope of the follwng claims.

I claim:

1. Method of separating components of a mixture by physical adsorption comprising contacting the mixture with a molecular sieve activated carbon in granular form for a time sufficient for the said activated carbon to adsorb and retain the readily adsorbable components of the mixture, wherein the said activated carbon is prepared by the successive steps of agglomerating pulverized charred naturally-occurring carbonaceous material with pitch, crushing the agglomerations thereof, activating the granular material thus obtained by treating it in a heating zone at from 300°C. to 400°C. for a period of at least 120 minutes with about 5 to 18 liters of air per gram of carbon, subsequently calcining it at a temperature of 850°C. to 960°C. for a period of 5 to 20 minutes, and recovering a granular, highly activated carbon having an iodine number of at least 450 and a carbontetrachloride number no greater than 2.

2. The method of claim 1 wherein the mixture is a mixture of hydrocarbons.

3. The method of claim 1 followed by recovering a selectively adsorbed component from the activated carbon.

* * * * *